United States Patent
Bingener-Casey et al.

(10) Patent No.: US 9,060,890 B2
(45) Date of Patent: Jun. 23, 2015

(54) MECHANICALLY ADJUSTABLE VARIABLE DIAMETER STENT

(75) Inventors: Juliane Bingener-Casey, Rochester, MN (US); Navtej S. Buttar, Rochester, MN (US); Louis-Michel Wong Kee Song, Rochester, MN (US)

(73) Assignee: Mayo Foundation For Medical Education and Research, Rochester, MN (US)

( * ) Notice: Subject to any disclaimer, the term of this patent is extended or adjusted under 35 U.S.C. 154(b) by 337 days.

(21) Appl. No.: 13/822,330

(22) PCT Filed: Sep. 15, 2011

(86) PCT No.: PCT/US2011/051733
§ 371 (c)(1),
(2), (4) Date: May 24, 2013

(87) PCT Pub. No.: WO2012/037327
PCT Pub. Date: Mar. 22, 2012

(65) Prior Publication Data
US 2013/0238079 A1    Sep. 12, 2013

Related U.S. Application Data

(60) Provisional application No. 61/383,587, filed on Sep. 16, 2010.

(51) Int. Cl.
*A61F 2/06* (2013.01)
*A61F 2/88* (2006.01)
(Continued)

(52) U.S. Cl.
CPC ... *A61F 2/88* (2013.01); *A61F 2/90* (2013.01); *A61F 2002/9534* (2013.01); *A61F 2250/0007* (2013.01); *A61F 2250/001* (2013.01)

(58) Field of Classification Search
CPC ............. A61F 2/88; A61F 2/885; A61F 2/95; A61F 2002/9534; A61F 2002/9505; A61F 2250/001; A61F 2250/0007
See application file for complete search history.

(56) References Cited

U.S. PATENT DOCUMENTS

| | | |
|---|---|---|
| 1,268,932 A | 6/1918 | Corrigan |
| 2,783,758 A | 3/1957 | Trott |
| 3,872,861 A | 3/1975 | Tamny et al. |

(Continued)

OTHER PUBLICATIONS

International Search Report and Written Opinion as mailed on Jan. 10, 2012 for International Application No. PCT/US2011/051733.

*Primary Examiner* — Jonathan W Miles
(74) *Attorney, Agent, or Firm* — Quarles & Brady LLP

(57) ABSTRACT

Methods and devices are disclosed for supporting and holding open a tubular structure in the body of an animal or human. In one form, the device is a manually adjustable variable outside diameter stent that can be repositioned or removed. The stent includes an elastic tubular body and an adjustment mechanism for the moving two ends of the body toward or away from each other. The elastic tubular body comprises a braiding of two groups of spaced apart helically wound elastic strands. The adjustment mechanism includes a bracket, a tension adjustor, and a tensioning wire attached to the bracket and the tension adjuster. The bracket and the tension adjuster are attached to one or more of the elastic strands of the two groups. Using the adjustment mechanism, the distance between the bracket and the tension adjustor can be decreased causing the outside diameter of the body to increase, or vice versa.

24 Claims, 2 Drawing Sheets

(51) Int. Cl.
*A61F 2/90* (2013.01)
*A61F 2/95* (2013.01)

(56) References Cited

U.S. PATENT DOCUMENTS

| | | | |
|---|---|---|---|
| 4,655,771 A | 4/1987 | Wallsten | |
| 4,923,458 A | 5/1990 | Fischer | |
| 4,954,126 A * | 9/1990 | Wallsten | 600/36 |
| 5,074,873 A | 12/1991 | Dioguardi | |
| 5,456,667 A * | 10/1995 | Ham et al. | 604/107 |
| 5,649,541 A | 7/1997 | Stuckey | |
| 5,776,142 A | 7/1998 | Gunderson | |
| 5,984,957 A * | 11/1999 | Laptewicz et al. | 623/1.15 |
| 6,238,431 B1 | 5/2001 | Asimacopoulos | |
| 6,468,298 B1 * | 10/2002 | Pelton | 623/1.11 |
| 7,211,109 B2 | 5/2007 | Thompson | |
| 7,458,938 B2 | 12/2008 | Patel et al. | |
| 8,425,549 B2 * | 4/2013 | Lenker et al. | 606/198 |
| 8,597,340 B2 * | 12/2013 | Anderson | 623/1.11 |
| 2003/0212450 A1 | 11/2003 | Schlick | |
| 2006/0190073 A1 | 8/2006 | Nachreiner et al. | |
| 2009/0061072 A1 * | 3/2009 | Isch et al. | 427/2.25 |
| 2009/0099640 A1 | 4/2009 | Weng | |
| 2009/0234428 A1 | 9/2009 | Snow et al. | |

* cited by examiner

MECHANICALLY ADJUSTABLE VARIABLE DIAMETER STENT

CROSS-REFERENCE TO RELATED APPLICATIONS

This application represents the national stage entry of PCT International Application No. PCT/US2011/051733 filed on Sep. 15, 2011, and claims priority from U.S. Provisional Patent Application No. 61/383,587 filed Sep. 16, 2010. The disclosure of each of these applications is hereby incorporated by reference as if set forth in their entirety herein.

STATEMENT REGARDING FEDERALLY SPONSORED RESEARCH

Not Applicable.

BACKGROUND OF THE INVENTION

1. Field of the Invention

The invention relates to methods and devices for supporting and holding open a tubular structure in the body of an animal or human. In particular, the invention relates to a stent that can be repositioned or removed once deployed.

2. Description of the Related Art

A stent is a device that can be placed within a body lumen for supporting and holding open a tubular structure in the body of an animal or human. In one common application, a stent is used for holding open a blood vessel. However, a stent can be used inside the lumen of any physiological conduit including arteries, veins, vessels, the biliary tree, the urinary tract, the alimentary tract, the tracheal bronchial tree, the genitourinary system, and the cerebral aqueduct.

Stents are generally tubular in structure and are radially expandable between an unexpanded insertion diameter and an expanded implantation diameter which is greater than the unexpanded insertion diameter. A stent is passed through the tubular structure in the body when collapsed, and then the stent will expand or can be expanded to its expanded implantation diameter after the implantation location has been reached.

Stents are generally categorized as being self-expanding, i.e., the stent expands by itself, or balloon expandable, i.e., the stent is expanded by a balloon inserted inside the stent. In one method for deploying a self-expanding stent, the stent is restrained within a sheath. After positioning of the self-expanding stent and sheath at the desired location in the lumen, the physician retracts the sheath to expose the stent and allow the stent to self-expand. In one method for deploying a balloon expandable stent, a delivery catheter assembly with an expandable balloon is used to deliver the stent. The stent is mounted on the balloon and the catheter assembly is pushed into the implantation site. Then, the balloon is inflated, radially applying a force inside the stent, and the stent is expanded to its expanded implantation diameter.

One problem with known stents is that they can be difficult to reposition or remove once deployed. Once a conventional stent is positioned in a particular tubular structure in the body and expanded in place, the stent cannot be reduced in diameter for repositioning or removal.

Thus, there exists a need for an improved stent that has an adjustable outside diameter such that the stent can be repositioned in, or removed from, a tubular structure in the body.

SUMMARY OF THE INVENTION

The present invention addresses the foregoing needs by providing a stent that has an adjustable outside diameter such that the stent can be repositioned in, or removed from, a tubular structure in the body. The stent includes an elastic tubular body and an adjustment mechanism for the moving the first end of the body toward or away from the second end of the body such that the outside diameter of the body increases when the first end of the body is moved towards the second end of the body, and such that the outside diameter of the body decreases when the first end of the body moves away from the second end of the body.

The elastic tubular body comprises a braiding of a first group of spaced apart helically wound first elastic strands and a second group of spaced apart helically wound second elastic strands. The adjustment mechanism includes a bracket, a tension adjustor, and a tensioning wire attached to the bracket and the tension adjustor such that the bracket and the tension adjustor are in spaced apart relationship. The bracket and the tension adjustor are attached to one or more of the first elastic strands and the second elastic strands. Using the adjustment mechanism, the distance between the bracket and the tension adjustor can be decreased causing the outside diameter of the body to increase, or the distance between the bracket and the tension adjustor can be increased causing the outside diameter of the body to decrease.

The tension adjustor can include a housing having a hole with internal threads that mate with an external threaded section of the tensioning wire, and the distance between the bracket and the tension adjustor can be varied by rotating the tensioning wire with respect to the hole. A distal end of the tensioning wire can be rotatably attached to the bracket. A proximal end of the tensioning wire can terminate in an enlarged head that is located within an interior space of the housing. The enlarged head of the tensioning wire can be structured to be engageable with a tool. The housing can include an opening, and the stent can further include a movable cover attached to the housing. The cover can include a first position in which the opening is closed off and a second position providing access to the end of the tensioning wire.

The stent can include a guide ring surrounding the tensioning wire. The guide ring can be attached to at least one of the first elastic strands and the second elastic strands, and the guide ring can be located between the bracket and the tension adjustor. The tensioning wire and the guide ring can contact at a bearing surface.

The bracket can be attached at an intersection of at least one of the first elastic strands and at least one of the second elastic strands, and the tension adjustor can be attached at an intersection of at least one of the first elastic strands and at least one of the second elastic strands. The first end of the body can be circumferential and the bracket can be attached to at least one of the first elastic strands and the second elastic strands comprising the first end of the body. The second end of the body can be circumferential and the tension adjustor can be attached to at least one of the first elastic strands and the second elastic strands comprising the second end of the body.

The stent can further include a second adjustment mechanism for the moving a first section of the body toward or away from the second section of the body. The second adjustment mechanism can include a second bracket, a second tension adjustor, and a second tensioning wire attached to the second bracket and the second tension adjustor such that the second bracket and the second tension adjustor are in spaced apart relationship. The second bracket can be attached to at least one of the first elastic strands and the second elastic strands, and the second tension adjustor can be attached to at least one of the first elastic strands and the second elastic strands. A distance between the second bracket and the second tension adjustor can be varied to move the first section of the body towards the second section of the body or to move the first section of the body away from the second section of the body.

In one form, the stent is a self-expanding stent. In another form, the stent is a balloon expandable stent.

In another aspect, the invention includes a tool for varying the distance between the bracket and the tension adjustor. After a stent is deployed to engage the inner surface of the tubular structure in the animal or human, the tool can be used to operate the tension adjustor to increase the distance between the bracket and the tension adjustor to move the first end of the body away from the second end of the body such that the outside diameter of the body decreases and disengages from the inner surface of the tubular structure in the animal or human. The stent can then be repositioned in a second location in the tubular structure, or removed from the tubular structure.

The tension adjustor can include a housing having a hole with internal threads that mate with an external threaded section of the tensioning wire, and the distance between the bracket and the tension adjustor can be varied by engaging the tensioning wire with the tool and rotating the tensioning wire with respect to the hole. A proximal end of the tensioning wire can terminate in an enlarged head that is located within an interior space of the housing, and the enlarged head of the tensioning wire can be structured to be engageable with a distal end of the tool.

The tool can include a cable suitable for insertion into the tubular structure in the animal or human, wherein the cable terminates in a tip for engaging the enlarged head of the tensioning wire. The tool can further include a sheath including a passageway having a distal opening, wherein the passageway is dimensioned for insertion of the cable such that the tip of the cable can protrude beyond the distal opening of the passageway.

In yet another aspect, the invention provides a method for positioning a stent in a tubular structure in an animal or human. The stent can include an elastic tubular body having a first end and an opposite second end and an outside diameter. The body can include a braiding of a first group of spaced apart helically wound first elastic strands and a second group of spaced apart helically wound second elastic strands such that the outside diameter of the body increases when the first end of the body is moved towards the second end of the body, and such that the outside diameter of the body decreases when the first end of the body moves away from the second end of the body. The stent can further include an adjustment mechanism for the moving the first end of the body toward or away from the second end of the body. The adjustment mechanism can include a bracket, a tension adjustor, and a tensioning wire attached to the bracket and the tension adjustor such that the bracket and the tension adjustor are in spaced apart relationship. The bracket can be attached to at least one of the first elastic strands and the second elastic strands, and the tension adjustor can be attached to at least one of the first elastic strands and the second elastic strands. The stent is positioned in the tubular structure in the animal or human, and the outside diameter of the body is caused to engage an inner surface of the tubular structure in the animal or human.

The tension adjustor can be used to decrease a distance between the bracket and the tension adjustor to move the first end of the body towards the second end of the body such that the outside diameter of the body increases and engages the inner surface of the tubular structure in the animal or human. The tension adjustor can be used to increase a distance between the bracket and the tension adjustor to move the first end of the body away from the second end of the body such that the outside diameter of the body decreases and disengages from the inner surface of the tubular structure in the animal or human. The stent can be repositioned in a second location in the tubular structure in the animal or human, and the outside diameter of the body can be caused to engage the inner surface of the tubular structure in the animal or human at the second location. Alternatively, the stent can be removed from the tubular structure in the animal or human after disengaging the stent from the inner surface of the tubular structure in the animal or human.

The stent can be caused to engage an inner surface of the tubular structure in the animal or human by restraining a self-expanding stent in a sheath and retracting the sheath such that the outside diameter of the body increases and engages the inner surface of the tubular structure in the animal or human.

The stent can be caused to engage an inner surface of the tubular structure in the animal or human by mounting a balloon expandable stent on a balloon and inflating the balloon such that the outside diameter of the body increases and engages the inner surface of the tubular structure in the animal or human.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
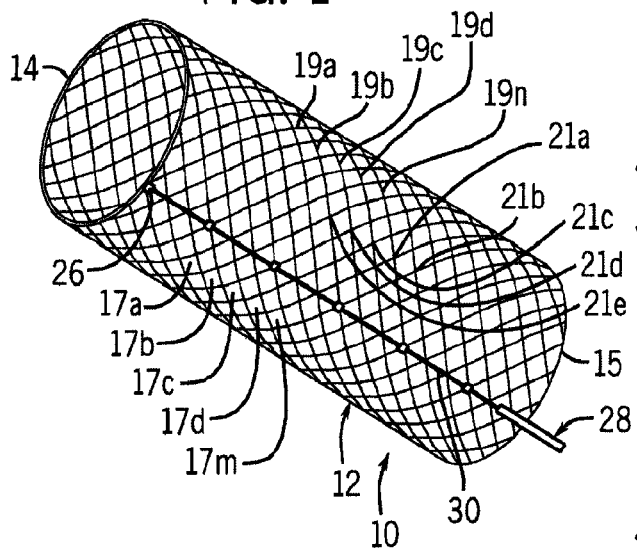
FIG. 1 is a perspective view of one embodiment of a stent according to the invention.

Looking first at FIG. 1, there is shown an example embodiment of a stent 10 according to the invention. The stent 10 includes an elastic tubular body 12 having a first circumferential end 14 and an opposite second circumferential end 16. The body is formed from a braiding of (i) a first group of spaced apart helically wound first elastic strands 17a, 17b, 17c, 17d to 17m where m varies depending on the desired spacing between the first elastic strands and the desired axial length of the body 12 and (ii) a second group of spaced apart helically wound second elastic strands 19a, 19b, 19c, 19d to 19n where n varies depending on the desired spacing between the second elastic strands and the desired axial length of the body 12. In the braiding, each strand can pass over one strand and then under the adjacent strand wound in the same direction.

The first elastic strands 17a, 17b, 17c, 17d to 17m and the second elastic strands 19a, 19b, 19c, 19d to 19n are helically wound with respect to a longitudinal axis defined by the tubular body 12 to create a braided configuration. The first elastic strands 17a, 17b, 17c, 17d to 17m and the second elastic strands 19a, 19b, 19c, 19d to 19n are helically wound in opposite directions to create intersections (such as 21a, 21b, 21c, 21d, 21e) of the first elastic strands 17a, 17b, 17c, 17d to 17m and the second elastic strands 19a, 19b, 19c, 19d to 19n. One or more of the first elastic strands 17a, 17b, 17c, 17d to 17m can form the first circumferential end 14 of the body 12, and one or more of the second elastic strands 19a, 19b, 19c, 19d to 19n can form the second circumferential end 16 of the body 12. The first elastic strands 17a, 17b, 17c, 17d to 17m and the second elastic strands 19a, 19b, 19c, 19d to 19n can be formed from a metallic material or a polymeric material. Example metallic materials include cobalt and chromium alloys, stainless steel, and nickel-titanium alloys.

Figure 5:
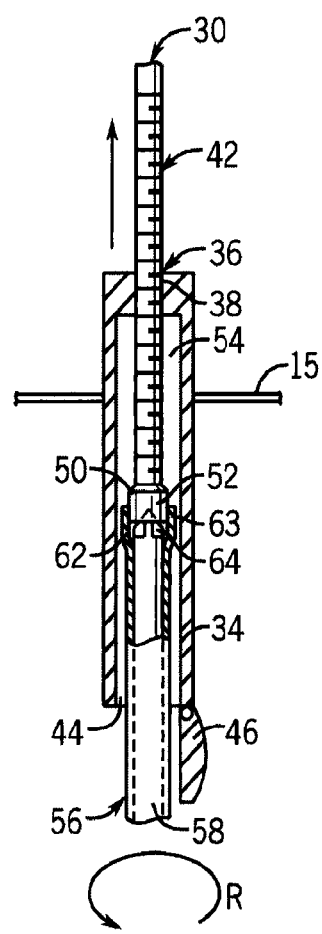
FIG. 5 is a detailed side view of a tension adjuster of the adjustment mechanism and a complementary tensioning tool of the stent of FIG. 1 shown partially in cross-section.
Figure 4:
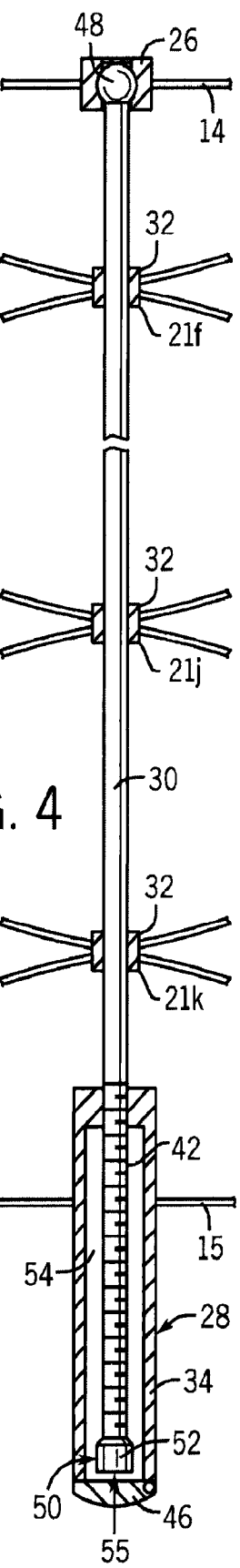
FIG. 4 is a side view of an adjustment mechanism of the stent of FIG. 1 shown partially in cross-section.

Referring to FIGS. 1, 4 and 5, the stent 10 includes an adjustment mechanism 24 for the moving the first end 14 of the body 12 toward or away from the second end 16 of the body 12 of the stent 10. The adjustment mechanism 24 includes a bracket 26, a tension adjustor 28 and a tensioning wire 30 that is attached to the bracket 26 and the tension adjustor 28. Guide rings 32 surround the tensioning wire 30 between the bracket 26 and the tension adjustor 28. In one embodiment, the bracket 26, the tension adjustor 28, the tensioning wire 30, and the guide rings 32 are formed from the same material as the first elastic strands 17a, 17b, 17c, 17d to 17m and the second elastic strands 19a, 19b, 19c, 19d to 19n.

In the embodiment of FIGS. 1 to 5, the bracket 26 is attached to an inner surface of the first circumferential end 14 of the body 12 using a suitable attachment method such as welding, heat sealing or gluing. The tension adjustor 28 is attached to an inner surface of the second circumferential end 16 of the body 12 using a suitable attachment method such as welding, heat sealing or gluing. The guide rings 32 are connected to an inner surface of intersections 21f, 21g, 21h, 21i, 21j and 21k using a suitable attachment method such as welding, heat sealing or gluing.

Referring now to FIGS. 4 and 5, the construction of the bracket 26, the tension adjustor 28 and the tensioning wire 30 can be explained in more detail. The tension adjustor 28 includes a housing 34 having a hole 36 with internal threads 38 that mate with an external threaded section 42 of the tensioning wire 30. The housing 34 includes an opening 44 that can be closed off with a hinged cover 46. The cover 46 prevents accumulation of debris in the housing 34. The tensioning wire 30 includes a spherical head 48 that is rotatably mounted in the bracket 26. A proximal end of the tensioning wire 30 terminates in an enlarged head 50 that is located within an interior space 54 of the housing 34. The enlarged head 50 of the tensioning wire 30 includes a hexagonal outer surface 52 and a socket 55.

Still referring to FIGS. 4 and 5, the stent 10 can be supplied with a tool 56 for varying the distance between the bracket 26 and the tension adjustor 28. The tool 56 includes a cable 58 suitable for insertion into the tubular structure in the animal or human. The cable 58 terminates in a tip 62 for engaging the enlarged head 50 of the tensioning wire 30. In the non-limiting example embodiment shown, the tip 62 of the tool 56 has an outer wall 63 for engaging the hexagonal outer surface 52 of the enlarged head 50 of the tensioning wire 30, and the tip 62 has a central protrusion 64 for engaging the central socket 55 of the enlarged head 50 of the tensioning wire 30. The tip 62 of the tool 56 and/or the enlarged head 50 of the tensioning wire 30 can be formed of materials that provide magnetic attraction between the tip 62 and the head 50. The tool 56 can be used with a sheath (not shown) that includes a passageway having a distal opening wherein the passageway is dimensioned for insertion of the cable 58 such that the tip 62 of the cable 58 can protrude beyond the distal opening of the passageway. The sheath is dimensioned for insertion into the tubular structure in the animal or human.

Having described the construction of the stent 10 and tool 56, the use of the stent 10 and tool 56 can be explained. A catheter having a first passageway and a second passageway can be introduced into the tubular structure in the animal or human. The stent 10 can be grasped by an endoscopic forceps, passed through the first passageway and then out of a distal end of the first passageway in the catheter, and positioned at a desired location in the tubular structure in the animal or human. The tool 56 is then passed through the second passageway in the catheter and then out of the distal end of the second passageway in the catheter. After opening the cover 46, the tip 62 of the tool 56 is then positioned to engage the hexagonal outer surface 52 of the enlarged head 50 of the tensioning wire 30 as shown in FIG. 5. In an alternative configuration of the tool, the tool is a multi-functional tool that also grasps the stent 10. This tool would only require a single passageway in the catheter.

Figure 3:
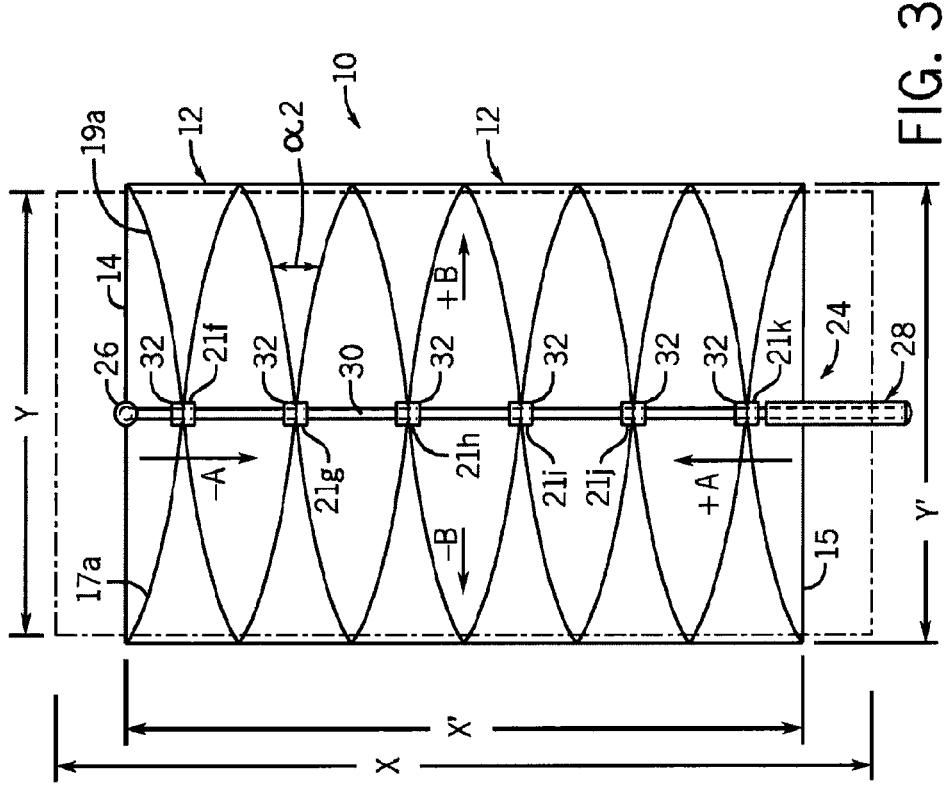
FIG. 3 is a side view of the stent of FIG. 1 in one expanded state.
Figure 2:
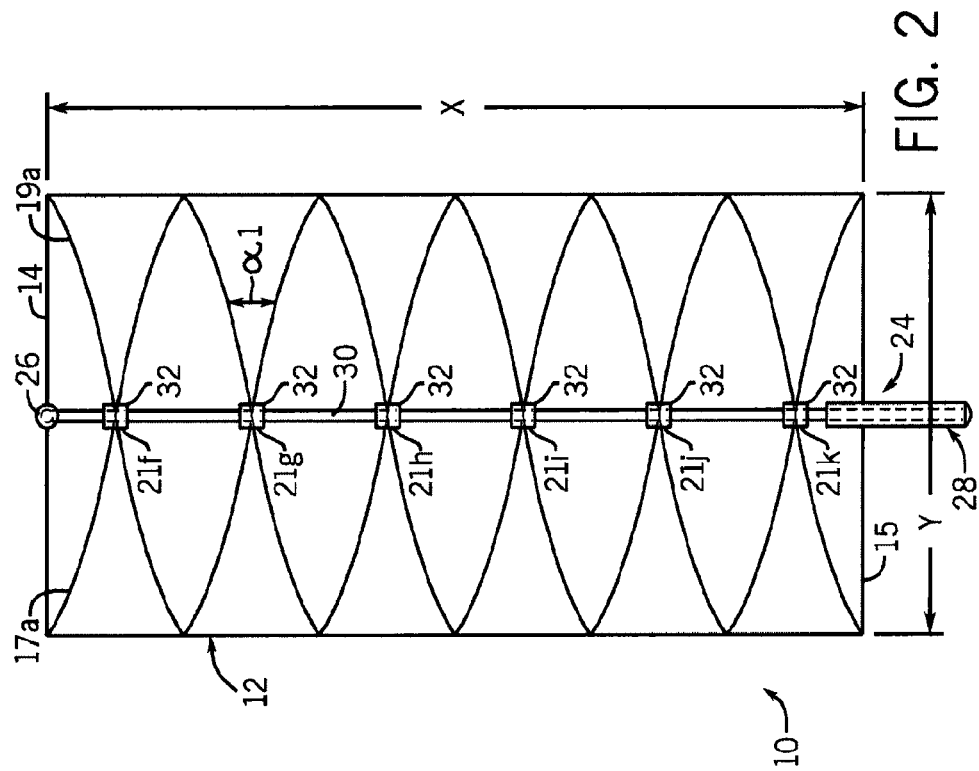
FIG. 2 is a side view of the stent of FIG. 1 in one unexpanded state.

When the stent 10 is first passed through the first passageway in the catheter and positioned at a desired location in the tubular structure in the animal or human, the stent 10 can have a configuration as shown in FIG. 2 in which the stent 10 has an axial length X and an outside diameter Y. With the tip 62 of the tool 56 engaging the hexagonal outer surface 52 of the enlarged head 50 of the tensioning wire 30 as shown in FIG. 5, the physician rotates the tool 56 in direction R in FIG. 5. Due to the engagement of the internal threads 38 of the housing 34 and the external threaded section 42 of the tensioning wire 30, rotation in direction R causes the tensioning wire 30 to move toward the opening 44 of the housing 34. As a result, the bracket 26 moves in direction −A and the tension adjustor 28 moves in direction +A as shown in FIG. 3. The guide rings 32 prevent any bowing of the tensioning wire 30 during movement of the tensioning wire 30.

Because the bracket 26 is attached to an inner surface of the first circumferential end 14 of the body 12 and the tension adjustor 28 is attached to an inner surface of the second circumferential end 16 of the body 12, the first circumferential end 14 and the second circumferential end 16 of the body 12 move toward each other. Due to the helically wound braided configuration of the first elastic strands 17a to 17m and the second elastic strands 19a to 19n, movement of the first circumferential end 14 and the second circumferential end 16 of the body 12 toward each other causes the stent 10 to move in directions −B and +B into the configuration as shown in FIG. 3 in which the stent 10 has an axial length X' and an outside diameter Y' (which can be compared to the configuration in which the stent 10 has an axial length X and an outside diameter Y as shown in FIG. 2 and as shown in dashed lines in FIG. 3). Note also how the outside diameter increases because the angle at the intersection of the strands decreases from $\alpha_1$ in FIG. 2 to $\alpha_2$ in FIG. 3. The increase in outside diameter from Y to Y' causes the outside diameter Y' of the body 12 of the stent 10 to engage the inner surface of the tubular structure in the animal or human. The cover 46 can then be closed.

When repositioning or removal of the stent 10 is desired, the catheter having the first passageway and the second passageway can be introduced into the tubular structure in the animal or human. The tool 56 is then passed through the second passageway in the catheter and then out of the distal end of the second passageway in the catheter. After opening the cover 46, the tip 62 of the tool 56 is then positioned to engage the hexagonal outer surface 52 of the enlarged head 50 of the tensioning wire 30 as shown in FIG. 5. With the tip 62 of the tool 56 engaging the hexagonal outer surface 52 of the enlarged head 50 of the tensioning wire 30 as shown in FIG. 5, the physician rotates the tool 56 in a direction opposite to direction R in FIG. 5. This causes the stent 10 to move back into the configuration as shown in FIG. 2 in which the stent 10 has an axial length X and an outside diameter Y. An endoscopic forceps is passed through the first passageway and then out of a distal end of the first passageway in the catheter, and the stent can be grasped for repositioning at another desired location, or removal from the tubular structure in the animal or human. After repositioning at another desired location, the outside diameter of the stent 10 can be enlarged for engagement with the inner surface of the tubular structure in the animal or human as described above.

When the stent 10 is a self-expanding stent, another method can be used. The stent 10 can be restrained within a sheath, passed through a passageway in a catheter, and positioned at a desired location in the tubular structure in the animal or human. The sheath can be retracted to expose the stent 10 and allow the stent 10 to self-expand to have the configuration as shown in FIG. 3 in which the stent 10 has an axial length X' and an outside diameter Y'. This causes the outside diameter of the body 12 of the stent 10 to engage an inner surface of the tubular structure in the animal or human. Thereafter, the stent 10 can be repositioned or removed as desired. Specifically, stent 10 can be caused to move back into the configuration as shown in FIG. 2 in which the stent 10 has an axial length X and an outside diameter Y and repositioned or removed as explained above.

When the stent 10 is a balloon expandable stent, another method can be used. A delivery catheter assembly with an expandable balloon is used. The stent 10 is mounted on the balloon and the catheter assembly is pushed into the implantation site. Then, the balloon is inflated, radially applying a force inside the stent 10, and the stent 10 is expanded to have the configuration as shown in FIG. 3 in which the stent 10 has an axial length X' and an outside diameter Y'. This causes the outside diameter of the body 12 of the stent 10 to engage an inner surface of the tubular structure in the animal or human. Thereafter, the stent 10 can be repositioned or removed as desired. Specifically, stent 10 can be caused to move back into the configuration as shown in FIG. 2 in which the stent 10 has an axial length X and an outside diameter Y and repositioned or removed as explained above.

Other arrangements of the bracket 26, the tension adjustor 28, the tensioning wire 30, and the guide rings 32 of the stent 10 are suitable. For example, the bracket 26 and the tension adjustor 28 can be attached at any of the intersections 21. The guide rings 32 can be omitted in certain embodiments. Also, more than one adjustment mechanism 24 including the bracket 26, the tension adjustor 28, and the tensioning wire 30 can be used. When using different numbers of adjustment mechanisms, one has the ability to manually adjust the outside diameter of either the whole stent or any part(s) of the stent.

Thus, the invention provides a manually adjustable variable outside diameter stent. The stent can be repositioned in, or removed from, a tubular structure in the body of an animal or human after being deployed.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A stent comprising:

an elastic tubular body having a first end and an opposite second end and an outside diameter, the body comprising a braiding of a first group of spaced apart helically wound first elastic strands and a second group of spaced apart helically wound second elastic strands such that the outside diameter of the body increases when the first end of the body is moved towards the second end of the body, and such that the outside diameter of the body decreases when the first end of the body moves away from the second end of the body; and an adjustment mechanism for the moving the first end of the body toward or away from the second end of the body, the adjustment mechanism including a bracket, a tension adjustor, and a tensioning wire attached to the bracket and the tension adjustor such that the bracket and the tension adjustor are in spaced apart relationship, the bracket being attached to at least one of the first elastic strands and the second elastic strands, the tension adjustor being attached to at least one of the first elastic strands and the second elastic strands, wherein a distance between the bracket and the tension adjustor can be varied to move the first end of the body towards the second end of the body or to move the first end of the body away from the second end of the body, and wherein the tension adjustor comprises a housing having a hole with internal threads that mate with an external threaded section of the tensioning wire, and wherein the distance between the bracket and the tension adjustor can be varied by rotating the tensioning wire with respect to the hole.

2. The stent of claim 1 wherein:

a distal end of the tensioning wire is rotatably attached to the bracket.

3. The stent of claim 2 wherein:

the enlarged head of the tensioning wire is structured to be engageable with a tool.

4. The stent of claim 2 wherein:

the housing includes an opening, and the stent further includes a movable cover attached to the housing, the cover including a first position in which the opening is closed off and a second position providing access to the end of the tensioning wire.

5. The stent of claim 1 wherein:

a proximal end of the tensioning wire terminates in an enlarged head that is located within an interior space of the housing.

6. The stent of claim 1 further comprising:

a guide ring surrounding the tensioning wire, the guide ring being attached to at least one of the first elastic strands and the second elastic strands, the guide ring being located between the bracket and the tension adjustor.

7. The stent of claim 6 wherein:

the tensioning wire and the guide ring contact at a bearing surface.

8. The stent of claim 1 wherein:

the bracket is attached at an intersection of at least one of the first elastic strands and at least one of the second elastic strands, and the tension adjustor is attached at an intersection of at least one of the first elastic strands and at least one of the second elastic strands.

9. The stent of claim 1 wherein:
the first end of the body is circumferential and the bracket is attached to at least one of the first elastic strands and the second elastic strands comprising the first end of the body.

10. The stent of claim 1 wherein:
the second end of the body is circumferential and the tension adjustor is attached to at least one of the first elastic strands and the second elastic strands comprising the second end of the body.

11. The stent of claim 1 further comprising:
a second adjustment mechanism for the moving a first section of the body toward or away from the second section of the body, the second adjustment mechanism including a second bracket, a second tension adjustor, and a second tensioning wire attached to the second bracket and the second tension adjustor such that the second bracket and the second tension adjustor are in spaced apart relationship, the second bracket being attached to at least one of the first elastic strands and the second elastic strands, the second tension adjustor being attached to at least one of the first elastic strands and the second elastic strands,
wherein a distance between the second bracket and the second tension adjustor can be varied to move the first section of the body towards the second section of the body or to move the first section of the body away from the second section of the body.

12. The stent of claim 1 wherein:
the stent is a self-expanding stent.

13. The stent of claim 1 wherein:
the stent is a balloon expandable stent.

14. A device for supporting and holding open a tubular structure in an animal or human, the device comprising:
the stent of claim 1; and
a tool for varying the distance between the bracket and the tension adjustor.

15. The device of claim 14 wherein:
a proximal end of the tensioning wire terminates in an enlarged head that is located within an interior space of the housing, and
the enlarged head of the tensioning wire is structured to be engageable with a distal end of the tool.

16. The device of claim 14 wherein:
the tool comprises a cable suitable for insertion into the tubular structure in the animal or human, the cable terminating in a tip for engaging the enlarged head of the tensioning wire.

17. The device of claim 16 wherein:
the tool further comprises a sheath including a passageway having a distal opening, the passageway being dimensioned for insertion of the cable such that the tip of the cable can protrude beyond the distal opening of the passageway.

18. A method for positioning a stent in a tubular structure in an animal or human, the method comprising:
(a) providing a stent comprising (i) an elastic tubular body having a first end and an opposite second end and an outside diameter, the body comprising a braiding of a first group of spaced apart helically wound first elastic strands and a second group of spaced apart helically wound second elastic strands such that the outside diameter of the body increases when the first end of the body is moved towards the second end of the body, and such that the outside diameter of the body decreases when the first end of the body moves away from the second end of the body; and (ii) an adjustment mechanism for the moving the first end of the body toward or away from the second end of the body, the adjustment mechanism including a bracket, a tension adjustor, and a tensioning wire attached to the bracket and the tension adjustor such that the bracket and the tension adjustor are in spaced apart relationship, the bracket being attached to at least one of the first elastic strands and the second elastic strands, the tension adjustor being attached to at least one of the first elastic strands and the second elastic strands wherein the tension adjustor comprises a housing having a hole with internal threads that mate with an external threaded section of the tensioning wire, and wherein the distance between the bracket and the tension adjustor can be varied by rotating the tensioning wire with respect to the hole;
(b) positioning the stent in the tubular structure in the animal or human; and
(c) causing the outside diameter of the body to engage an inner surface of the tubular structure in the animal or human.

19. The method of claim 18 wherein:
step (c) comprises using the tension adjustor to decrease a distance between the bracket and the tension adjustor to move the first end of the body towards the second end of the body such that the outside diameter of the body increases and engages the inner surface of the tubular structure in the animal or human.

20. The method of claim 18 further comprising:
(d) using the tension adjustor to increase a distance between the bracket and the tension adjustor to move the first end of the body away from the second end of the body such that the outside diameter of the body decreases and disengages from the inner surface of the tubular structure in the animal or human.

21. The method of claim 20 further comprising:
(e) repositioning the stent in a second location in the tubular structure in the animal or human; and
(f) causing the outside diameter of the body to engage the inner surface of the tubular structure in the animal or human at the second location.

22. The method of claim 20 further comprising:
(e) removing the stent from the tubular structure in the animal or human.

23. The method of claim 18 wherein:
step (c) comprises restraining the stent in a sheath and retracting the sheath such that the outside diameter of the body increases and engages the inner surface of the tubular structure in the animal or human.

24. The method of claim 18 wherein:
step (c) comprises mounting the stent on a balloon and inflating the balloon such that the outside diameter of the body increases and engages the inner surface of the tubular structure in the animal or human.

* * * * *